US012669501B2

(12) United States Patent
Lei et al.

(10) Patent No.: US 12,669,501 B2
(45) Date of Patent: Jun. 30, 2026

(54) DEVICE FOR DETECTING AN ANALYTE IN A SAMPLE

(71) Applicant: Zhejiang Orient Gene Biotech Co., Ltd, Huzhou (CN)

(72) Inventors: Siyu Lei, Huzhou (CN); Jianqiu Fang, Huzhou (CN); Hua Zhang, Huzhou (CN); Guoliang Yuan, Huzhou (CN)

(73) Assignee: ZHEJIANG ORIENT GENE BIOTECH CO., LTD, Zhejiang (CN)

( * ) Notice: Subject to any disclaimer, the term of this patent is extended or adjusted under 35 U.S.C. 154(b) by 815 days.

(21) Appl. No.: 17/879,564

(22) Filed: Aug. 2, 2022

(65) Prior Publication Data

US 2023/0294098 A1 Sep. 21, 2023

Related U.S. Application Data

(60) Provisional application No. 63/333,299, filed on Apr. 21, 2022, provisional application No. 63/327,048, filed on Apr. 4, 2022.

(30) Foreign Application Priority Data

Mar. 15, 2022 (CN) .......................... 202210254433.4
Apr. 11, 2022 (CN) .......................... 202210377142.4

(51) Int. Cl.
*B01L 3/00* (2006.01)
*A61B 10/00* (2006.01)
(Continued)

(52) U.S. Cl.
CPC ... *G01N 33/54388* (2021.08); *A61B 10/0051* (2013.01); *A61B 10/0096* (2013.01); *B01L 3/5023* (2013.01); *B01L 3/5029* (2013.01);

*B01L 9/00* (2013.01); *G01N 1/10* (2013.01); *G01N 33/56983* (2013.01);
(Continued)

(58) Field of Classification Search
CPC ............ A61B 10/0051; A61B 10/0096; B01L 2300/0681; B01L 2300/0825; B01L 2300/0832; B01L 2300/126; B01L 2400/0406; B01L 3/5023; B01L 3/5029; B01L 9/00; B01L 9/52; G01N 1/10; G01N 2001/1056; G01N 2333/165; G01N 33/54388; G01N 33/56983
See application file for complete search history.

(56) References Cited

U.S. PATENT DOCUMENTS 4,857,453 A 8/1989 Ullman et al.
5,073,484 A 12/1991 Swanson et al.
(Continued)

FOREIGN PATENT DOCUMENTS

AU 2004226798 10/2004
JP 4579902 11/2010

*Primary Examiner* — Benjamin R Whatley
(74) *Attorney, Agent, or Firm* — MUNCY, GEISSLER, OLDS & LOWE, P.C.

(57) ABSTRACT

The present invention provides a device for detecting an analyte in a sample, including a chamber for receiving a testing element, where the testing element has a first position and a second position in the chamber; the testing element is not in contact with a fluid sample when the testing element is located in the first position, and the testing element is in contact with a fluid sample when the testing element is located in the second position.

13 Claims, 12 Drawing Sheets

(51) Int. Cl.
    *B01L 9/00*          (2006.01)
    *G01N 1/10*          (2006.01)
    *G01N 33/543*      (2006.01)
    *G01N 33/569*      (2006.01)

(52) U.S. Cl.
    CPC .................. *B01L 2300/0825* (2013.01); *B01L 2400/0406* (2013.01); *G01N 2001/1056* (2013.01); *G01N 2333/165* (2013.01)

(56) References Cited

U.S. PATENT DOCUMENTS

| | | | |
|---|---|---|---|
| 5,119,831 | A | 6/1992 | Robin et al. |
| 5,185,127 | A | 2/1993 | Vonk |
| 5,275,785 | A | 1/1994 | May et al. |
| 5,352,410 | A | 10/1994 | Hansen et al. |
| 5,376,337 | A | 12/1994 | Seymour |
| 5,416,000 | A | 5/1995 | Allen et al. |
| 5,504,013 | A | 4/1996 | Senior |
| 5,576,009 | A | 11/1996 | Nastke et al. |
| 5,602,040 | A | 2/1997 | May et al. |
| 5,622,871 | A | 4/1997 | May et al. |
| 5,654,162 | A | 8/1997 | Guire et al. |
| 5,656,503 | A | 8/1997 | May et al. |
| 5,686,315 | A | 11/1997 | Pronovost et al. |
| 5,766,961 | A | 6/1998 | Pawlak et al. |
| 5,770,460 | A | 6/1998 | Pawlak et al. |
| 5,916,815 | A | 6/1999 | Lappe |
| 5,976,895 | A | 11/1999 | Cipkowski |
| 6,140,136 | A | 10/2000 | Lee |
| 6,187,269 | B1 | 2/2001 | Lances et al. |
| 6,187,598 | B1 | 2/2001 | May et al. |
| 6,228,660 | B1 | 5/2001 | May et al. |
| 6,235,241 | B1 | 5/2001 | Catt et al. |
| 6,248,598 | B1 | 6/2001 | Bogema |
| 6,306,642 | B1 | 10/2001 | Nelson et al. |
| 6,352,862 | B1 | 3/2002 | Davis et al. |
| 6,372,515 | B1 | 4/2002 | Casterlin et al. |
| 6,379,620 | B1 | 4/2002 | Tydings et al. |
| 6,403,383 | B1 | 6/2002 | Casterlin et al. |
| 8,114,027 | B2 | 2/2012 | Triva |
| 8,317,728 | B2 | 11/2012 | Triva |
| 8,979,784 | B2 | 3/2015 | Triva |
| 9,011,358 | B2 | 4/2015 | Triva |
| 9,173,779 | B2 | 11/2015 | Triva |
| 10,327,741 | B2 | 6/2019 | Triva |
| 2021/0402398 | A1* | 12/2021 | Rothberg .............. B01L 3/5023 |
| 2022/0065847 | A1* | 3/2022 | Hasan .............. A61B 5/150358 |
| 2022/0395259 | A1* | 12/2022 | Thakor .............. A61B 10/0291 |

* cited by examiner

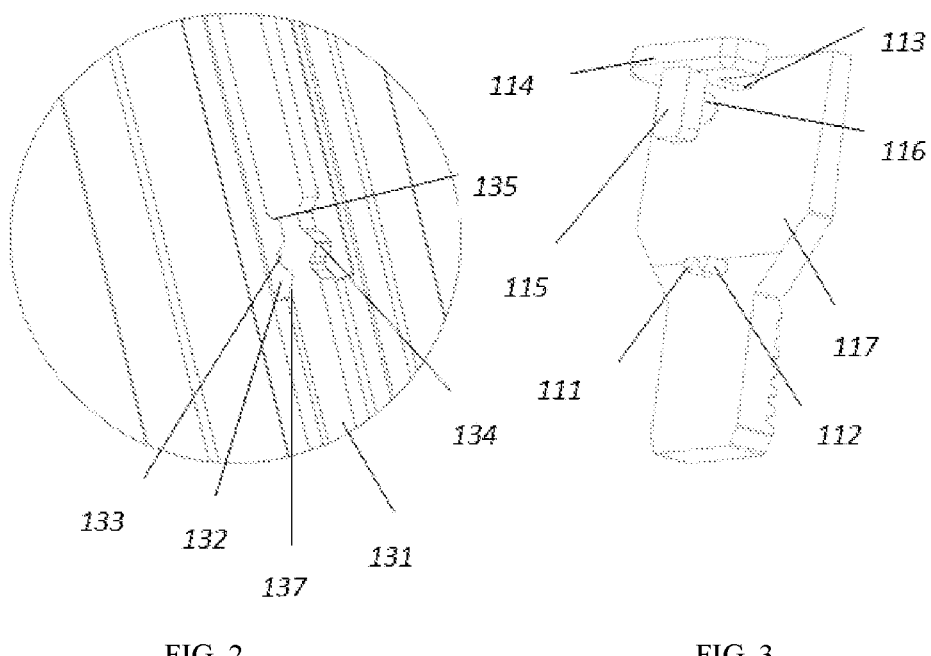
FIG. 2                                FIG. 3

DEVICE FOR DETECTING AN ANALYTE IN A SAMPLE

CROSS-REFERENCE TO RELATED APPLICATIONS

The present application claims priority to a Chinese prior application No. 2022103771424 and filed on Apr. 11, 2022, a Chinese prior application No. 2022102544334 and filed on Mar. 15, 2022, as well as a US prior provisional application No. 63/333,299 and filed on Apr. 21, 2022, and a US prior provisional application No. 63/327,048 and filed on Apr. 4, 2022; the entire contents of the above application, including the description, accompanying drawings and claims of which are incorporated herein as a portion of the present invention.

TECHNICAL FIELD

The present invention relates to a device for collecting and detecting a liquid sample, in particular, a device for collecting and detecting an analyte in a liquid sample in the field of rapid diagnosis, such as a urine and saliva collection and test device.

BACKGROUND

The following description is merely an introduction to the background art and not to limit the present invention.

At present, the test device for detecting the presence or absence of an analyte in sample is widely used in hospitals or homes, and such device for rapid diagnosis comprises one or more test strips, such as early pregnancy detection, drug abuse detection, etc. The apparatus is very convenient, and the detection result can be obtained from the test strip after one minute or no more than ten minutes.

The drug detection is widely used by drug control department, Public Security Bureau, drug rehabilitation centers, physical examination centers, the national conscription offices, etc. The drug detection is diverse and frequent. Some detections need to collect samples and then samples are detected in professional testing agency or testing laboratories, and some detections needs to be completed in the site in time, for example, roadsides, for example, persons who drive after drug use need to be tested on the spot (referred to as "Drug Driving"), to obtain the results in time. For example, the detection of saliva samples is gradually accepted and favored by testing agencies or testing personnel due to convenient collection. In some literatures, various sample collection and test devices for clinical and domestic uses have been obtained and described. For example, the U.S. Pat. No. 5,376,337 discloses a saliva sampling device in which a piece of filter paper is used to collect saliva from the mouth of a subject and deliver saliva to an indicator reagent. The U.S. Pat. Nos. 5,576,009 and 5,352,410 have disclosed a syringe-type fluid sampling device.

Moreover, with the transmission of infectious diseases in recent years, in particular to coronavirus, household self-inspection has become mainstream products. Household self-inspection is convenient for sampling and friendly in operation, and can prevent the contamination to the environment due to sampling. It is more demanding for household self-inspection products.

In view of the above technical problems in some conventional products, it is necessary to improve them and provide an alternative approach to solve the drawbacks of the prior art, thus satisfying the ever-increasing demands for in vitro diagnosis, in particular to the demands for the household self-inspection market.

SUMMARY OF THE INVENTION

Directed to the above situation, to overcome the shortcomings in the prior art, the objective of the present invention is to provide a device for detecting an analyte in a fluid sample, and a receiving device which is matched with the test device and used for receiving the test device. The receiving device includes a chamber, and the chamber includes a liquid chamber for holding a liquid and an inserting chamber for a testing element to insert. The "receiving" in the receiving device is not construed as limiting the specific purpose of the device; the receiving device may be called a liquid treatment and mixing device, and also may be called a liquid sample conveying and transferring device and thus, may be called a device.

A first aspect of the present invention to provides a device for detecting an analyte, including a chamber for receiving a testing element, where the testing element has a first position and a second position in the chamber; the testing element is not in contact with a fluid sample when the testing element is located in the first position, and the testing element is in contact with a fluid sample when the testing element is located in the second position.

In some detailed embodiments, the chamber for receiving the testing element is further provided with a collector for collecting a fluid sample collector, and the collector is disposed on one end of the chamber. In some embodiments, the sample collector may be in detachable combination with the chamber. In some embodiments, the sample collector is a sponge swab or flocking swab for collecting the fluid sample. In some embodiments, the sample collected by the collector may not or will not flow onto the testing element. In some embodiments, the collector is treated, mixed or eluted by a solution located in the chamber: a portion of the testing element is allowed to enter the receiving device to contact liquid, thereby completing the detection. In some embodiments, the portion of the testing element includes sample receiving are or a sample application cushion of the testing element.

In some embodiments, the chamber for receiving the testing element further includes a carrier used for bearing the testing element; the carrier has a first position and a second position in the chamber; and the carrier drives the testing element to change or move between the first position and the second position.

In some preferred embodiments, the device further includes a movable element, and the movable element is connected to the chamber for receiving the testing element via a locking structure. The term "connect" herein refers to the connection in a relatively fixed position; in case of being in a locking state, the movable element is fixed on a relatively fixed position of the chamber; in case of being unlocked state, the movable element may move or slide on the chamber. The way of sliding refers to sliding from the first position to the second position. In some embodiments, the movable element is connected with the carrier; when the movable element is located in a locking position, the carrier may not move relative to the chamber for receiving the testing element. In some other embodiments, when the locking structure is unlocked, the movable element may move relative to the chamber for receiving the testing element, thus driving the carrier to move. In some embodiments, when the carrier is located in the first position, the carrier is fixed on or in the chamber for receiving the testing element by the locking structure: after being unlocked, the carrier is allowed to move from the first position to the second position by moving the locking structure. In some embodiments, when the carrier is located in the first position, the movable element is fixed on or in the chamber for receiving the testing element by the locking structure: after being unlocked, the carrier is allowed to move from the first position to the second position by moving the movable element.

In some embodiments, when the carrier is located in the first position, the testing element on the carrier is not in contact with a fluid sample; when the carrier is located in a second position, the carrier is in contact with a fluid sample such that the testing element is in contact with the fluid sample. In this way, the fluid sample flows on the testing element such that the test result may be read out on the testing area of the testing element.

In some embodiments, the locking structure includes one or more bolt structures: the chamber for receiving the testing element includes one or more notched structures for receiving the bolt; the bolt is inserted into the notch to be fixed or locked in a locking state. In some embodiments, the movable element is provided with a bolt having a locking structure; the chamber for receiving the testing element has a notch for receiving the bolt.

The movable element is located in the first position with the chamber via the locking structure, and after being unlocked, the movable element may slide relative to the chamber.

In some embodiments, the movable element includes a connecting piece integrally connected with the carrier and a portion of the locking structure. In some embodiments, the sliding piece of the locking structure may slide on a sliding groove of the chamber. In some embodiments, the sliding may drive the carrier to slide or move from the first position to the second position. In some embodiments, the portion of the locking structure is located on the sliding groove of the chamber.

The so-called "locking structure" includes at least two functions, namely, a locking function and unlocking function. The locking function may directly or indirectly enable the carrier to be fixed relative to the chamber for receiving the testing element. After being unlocked, the carrier is directly or indirectly allowed to be not fixed relative to the chamber for receiving the testing element, that is, capable of achieving mutual or relative movement. When there is a movable element, the movable element includes a portion of the locking structure; and the chamber for receiving the testing element includes another portion of the locking structure; these two portions are matched to complete the locking state or unlocking state.

In some embodiments, the portion of the locking structure is located on the sliding groove of the chamber. In some embodiments, the portion of the locking structure located on the sliding groove includes notches disposed relatively. In some embodiments, the portion of the locking structure is located on the movable element, and the locking structure located on the movable element includes two bolts: when the movable element is located in the locking position, the two bolts are received by the two notches: when the movable element is unlocked, the two bolts are separated from the notches such that the movable element is capable of moving from the first position to the second position. In some embodiments, the movable element includes a sliding rail, and the sliding rail moves in the sliding groove to drive the carrier to move.

In some embodiments, the movable element is a sheet structure, and the sheet structure includes a first face and a second face; the sliding rail is located on the first face and connected with a positioning piece. The positioning piece is connected with the sliding rail; the sliding rail drives the positioning piece to move in the chamber. In some embodiments, the positioning piece is located in the chamber, and the sliding rail is connected with the sheet-like movable element, and the sheet-like movable element is located on an outer surface of the chamber. In some embodiments, the sliding groove on the chamber is located between the positioning piece and the sheet-like movable element, and the sliding rail passes through the sliding groove.

In some embodiments, the sliding groove is formed by opening on the side wall of the chamber, and has a preset distance; the distance is the moving distance of the movable element from the first position to the second position.

In some embodiments, an insertion piece is further connected with the positioning piece; the insertion piece is inserted into a receiving opening of the carrier, thus achieving the fixed connection between the carrier and the movable element.

In some embodiments, the receiving chamber includes a solution reagent for treating a sample. In some embodiments, the sample collector is allowed to flow into the receiving chamber firstly, and then a portion of the carrier flows into the receiving chamber.

In some embodiments, the apparatus further includes a receiving chamber for receiving the insertion of the collector, and the receiving chamber is independent of a chamber for holding the testing element. In some embodiments, the chamber for receiving the collector may be further used for receiving a portion of the testing element. In some embodiments, the chamber for receiving collector may be further used for receiving a sample application area of the testing element. In some embodiments, the receiving chamber includes a reagent for treating a fluid sample. In some embodiments, the testing element is inserted into or enters into, or has been located in the receiving chamber when the testing element is located in the second position. In some embodiments, a solution reagent is sealed in the receiving chamber in advance. In some embodiments, the sample application area of the testing element is located on the carrier; when the carrier is located in the second position, the sample application area located on the carrier enters into the receiving chamber to be in contact with the fluid sample.

In some embodiments, the carrier may still return to the first position and is fixed on the first position after being located in the second position. When the carrier returns to the first position, test results on the testing element may be read out. Alternatively, when the testing element or carrier is located in the second position, the test result is read out at the testing area. In some embodiments, the chamber for receiving the testing element includes a window used for reading a test result. When the testing element moves to the second position from the first position, the testing area is located under the window. In some embodiments, the sample is saliva, nasal mucus and throat mucus. In some embodiments, the analyte is virus, bacterium or a drug small molecule.

On the other hand, the present invention provides a method for detecting an analyte in a sample and the method includes:

providing a chamber used for accommodating a testing element; the testing element has a locked first position and an unlocked second position in the chamber; the testing element may be moved to the second position from the first position.

In case of being in the first position, the testing element is not in contact with a fluid sample; in case of being in the second position, the testing element is in contact with a fluid sample.

In some embodiments, the chamber for receiving the testing element further includes a collector for collecting a fluid sample.

In some embodiments, provided is an accommodating chamber, used for combining or linking with the chamber for accommodating the testing element such that the collector is inserted into the accommodating chamber. In some embodiments, the collector is first inserted into the accommodating chamber, and then the testing element moves to the second position from the first position: a portion of the testing element is inserted into or enters to the accommodating chamber, or the sample application area is inserted into or enters to the accommodating chamber. The testing element enters to the accommodating chamber to contact with the sample, thus detecting or testing the analyte.

In some embodiments, the collector is inserted into the accommodating chamber. The treatment solution in the accommodating chamber is in contact with the collector, thus dissolving, lysing and washing the sample on the collector. The sample is mixed with the treatment solution.

In some embodiments, before the collector is inserted into the accommodating chamber, a treatment solution is sealed in the accommodating chamber. In some embodiments, before being inserted into the accommodating chamber, the collector is used to collect a fluid sample, for example, saliva, sweat, blood, urine, sputum or nasal secretion.

In some embodiments, the testing element is locked in the first position and unlocked in the second position such that the testing element moves to the initial first position from the second position and is locked.

In some embodiments, the device further includes a movable element, and the movable element drives the testing element to move from the first locking position to the second position. In some embodiments, the testing element is disposed on the carrier and the movable element drives the carrier to move from the first position to the second position. The movable element and the chamber for accommodating the testing element have a first locking position and a second position such that the movable element has a first locking position and a second position in the chamber for accommodating the testing element. In some embodiments, the second position may be or may not be a locking position.

In some embodiments, the movable element is fixed during the process of moving to the second position from the first position. In some embodiments, the movable element is sleeved outside the chamber for receiving the testing element; the testing element or the carrier is located in the chamber for receiving the testing element.

In some embodiments, the movable element includes a locking bolt locked with the chamber for accommodating the testing element, and a sliding rail which slides on the chamber for receiving the testing element; the locking bolt and the chamber or a testing chamber may be in a locking state.

Beneficial Effects

The above structure can be used to achieve the self-detection in a family. The present invention is easy to operate and not prone to making mistakes, and can lower environmental pollution and drop damage to operators.

BRIEF DESCRIPTION OF DRAWINGS

FIG. 2 is an enlarged diagram showing a portion of structure in a detailed embodiment of the present invention;

FIG. 3 is an enlarged diagram showing a movable element in a detailed embodiment of the present invention;

DETAILED DESCRIPTION OF EMBODIMENTS

Figure 1:
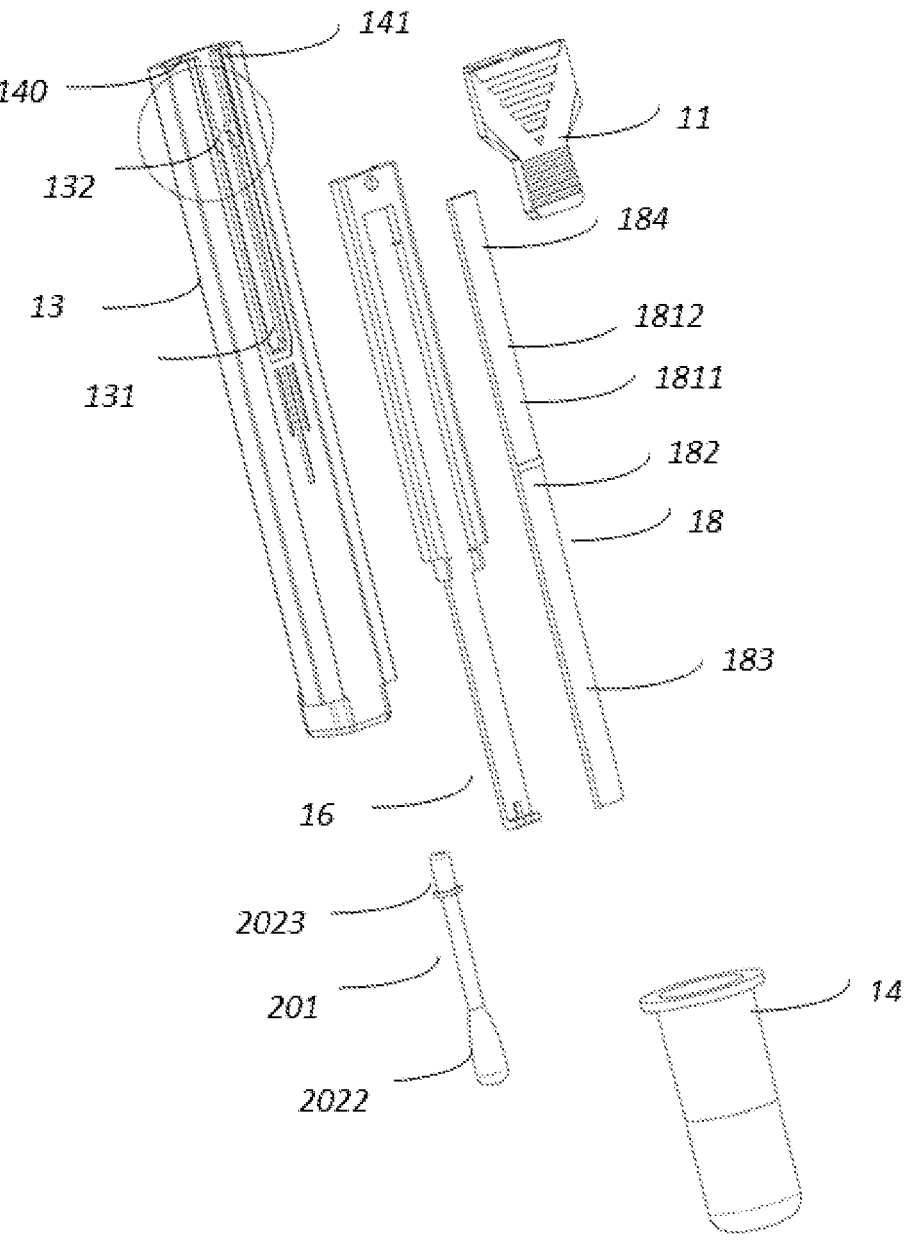
FIG. 1 is a schematic diagram showing a disassembled three-dimensional structure of a package assembly in a detailed embodiment of the present invention.

The structures or technical terms used in the present invention are further described in the following. Unless otherwise indicated, they are understood or interpreted according to ordinary terms and definitions in the art.

Detection

Detection denotes assaying or testing whether a substance or material exists, for example, but not limited to, chemicals, organic compounds, inorganic compounds, metabolites, drugs or drug metabolites, organic tissues or metabolites of organic tissues, nucleic acid, proteins or polymers. Moreover, detection denotes testing the number of a substance or material. Further, assay also denotes immunoassay, chemical detection, enzyme detection and the like.

Samples

The samples that can be detected by the test device or collected by the collector of the present invention include biological liquid (e.g. case liquid or clinical samples). Liquid samples or fluid specimens may be derived from solid or semi-solid samples, including excreta, biological tissues and food samples. Solid or semi-solid samples are transformed into liquid samples by any proper method, for example, mixed, mashed, macerated, incubated, dissolved into a proper solution (for example, water, phosphate solution or other buffer solutions), and solid samples are digested by zymolysis. "Biological samples" include samples from animals, plants and food, for example, including urine, saliva, blood and components thereof, spinal fluid, vaginal secretion, semen, faeces, sweat, secreta, tissues, organs, tumors, cultures of tissues and organs, cell culture and medium from human or animals. The preferred biological sample is urine, preferably, the biological sample is saliva, sputum, nasal secretion, and the like. Food samples include substances processed from food, final products, meat, cheese, wine, milk and drinking water. Plant samples are derived from any plants, plant tissues, plant cell cultures and media. "Environmental samples" are derived from the environment (for example, liquid samples, wastewater samples, soil texture samples, underground water, seawater and effluent samples from lakes and other water bodies). Environmental samples may further include sewage or other waste water.

Any analyte can be detected using the appropriate detecting element or testing element of the present invention. Preferably, the present invention is used to detect small drug molecules in saliva and urines. Preferably, the present invention is used to detect virus, bacteria and other small molecules in saliva, throat or nasal cavity fluid. Any form of samples above, either initially solid or liquid, can be collected by the collector 201 in the present invention, as long as the liquid or liquid samples can be absorbed by the absorbing element; and the absorbing element 2022 is generally located on the collector. The absorbing element 2022 here is generally prepared from a water absorbent material and is initially dry. It can absorb liquid or fluid samples by capillary or other characteristics of the absorbing element material, so as to keep the fluid samples in the absorbing element. The absorbent material can be any liquid absorbing material such as sponge, filter paper, polyester fiber, gel, non-woven fabric, cotton, polyester film, yarn, flocking, etc. When a flocking swab is taken, the flocking swab described in the following patents may be used to collect the fluid samples as a part of the present invention; U.S. Pat. Nos. 8,114,027, 8,317,728, 8,979,784, 9,011,358, 9,173,779, 10,327,741, AU2004226798, JP4579902 and ZL200610099310.9. In some embodiments, the absorbing element 2022 is hard when it is dry, for example, a sponge becomes soft when it is wet, and can be compressed after softening to release liquid. Of course, when it is a relatively sparse sponge, for example, a sponge swab, liquid samples can be still absorbed in a little amount, for example, 5-100 μL: for example, a sponge swab described in a U.S. provisional application 63/300,811 with application number: Jan. 19, 2022 may be also used in this present invention as a detailed example of the collector.

Of course, the absorbing element is not necessarily prepared by an absorbent material but may be prepared by a non-water absorbent material. But the absorbing element has pores, threads, and cavities, and samples may be collected on these structures. These samples are generally solid or semi-solid samples, and are filled between threads, or in cavities or holes, thus collecting the samples. Of course, optionally, the absorbing element may consist of some non-water absorbent fibers and hairs; these materials are used to scratch solid, semi-solid or liquid samples such that these samples are maintained on the absorbing element.

Downstream and Upstream

Downstream or upstream is divided according to a flow direction of a liquid, generally, a liquid or fluid flows to a downstream area from an upstream area. The downstream area receives the liquid from the upstream area, and a liquid also may flow to a downstream area along an upstream area. Here, downstream or upstream is generally divided according to a flow direction of a liquid, for example, on some materials where capillary force is utilized to promote the flow of a liquid, a liquid may overcome gravity to flow towards an opposite direction to the gravity; and at this time, downstream or upstream is divided according to a flow direction of the liquid. For example, as shown in FIG. 1, the testing element 18 mentioned herein has a sample application area 183, a labeled area 182, a testing area 181 and an absorption area 184. The sample application area 183 is located upstream of the labeled area 182, and the testing area 181 is located downstream of the labeled area, and the absorption area is located downstream of the testing area. Generally, a fluid flows to the downstream from the upstream along the flow direction of the testing element. In a detailed embodiment of the present invention, when the testing device is vertical, for example, as shown in FIG. 1, a liquid sample will overcome gravity due to capillary force to flow from bottom to top, namely, flowing to the downstream from the upstream once contacts the sample application area 183. In this way, the liquid sample flows through the labeled area 182, and then to the testing area 181, and finally flows to a water absorbing area.

Of course, the upstream and the upstream here may be also a motion trail or direction of an object instead of a circulation direction of a liquid. For example, in the operating process, after the chamber 14 containing a treatment agent is inserted by an absorber, the chamber is bonded with the chamber with a testing element at this time: then the treatment solution in the container contacts the sampling element 201 in the collector to treat the sample. For example, the sample is dissolved, lysed, eluted and the like, and at this time, the testing element located in the chamber is in the initial position. When a sample needs to be detected, it is unlocked such that the testing element 18 or the carrier 16 bearing the testing element can slide within the chamber, thus moving to the second position from the first position. In case of being in the second position, the testing element stretches out from one end of the container chamber 13, for example, stretches out of the chamber with the sample application area into the chamber 101 containing the treatment reagent directly to contact a liquid or a mixture of liquid samples, thus completing the testing or detection.

Gas Flow or Liquid Flow

Gas flow or liquid flow means that liquid or gas can flow from one place to another place. The flow process may pass through some physical structures, to play a guiding role. The "passing through some physical structures" here means that liquid passes through the surface of these physical structures or their internal space and flows to another place passively or actively, where passivity is usually caused by external forces, such as the flow of the capillary action and air pressure action. The flow here may also be a flow due to self-action (gravity or pressure) of the liquid or gas, and also may be a passive flow. The fluid under the action of air pressure may be a forward flow, or also a reverse flow; or a fluid is urged to flow to another position from a position under the action of air pressure. Here, the flow does not mean that a liquid or a gas is necessarily present, but indicates a relationship or state between two objects under some circumstances. In case of presence of liquid, it can flow from one object to another. Here it means the state in which two objects are connected. In contrast, if there exists no gas flow or liquid flow state between two objects, and liquid exists in or above one object but cannot flow into or on another object, it is a non-flow, non-liquid or non-gas flow state.

Detachable Combination

Figure 9:
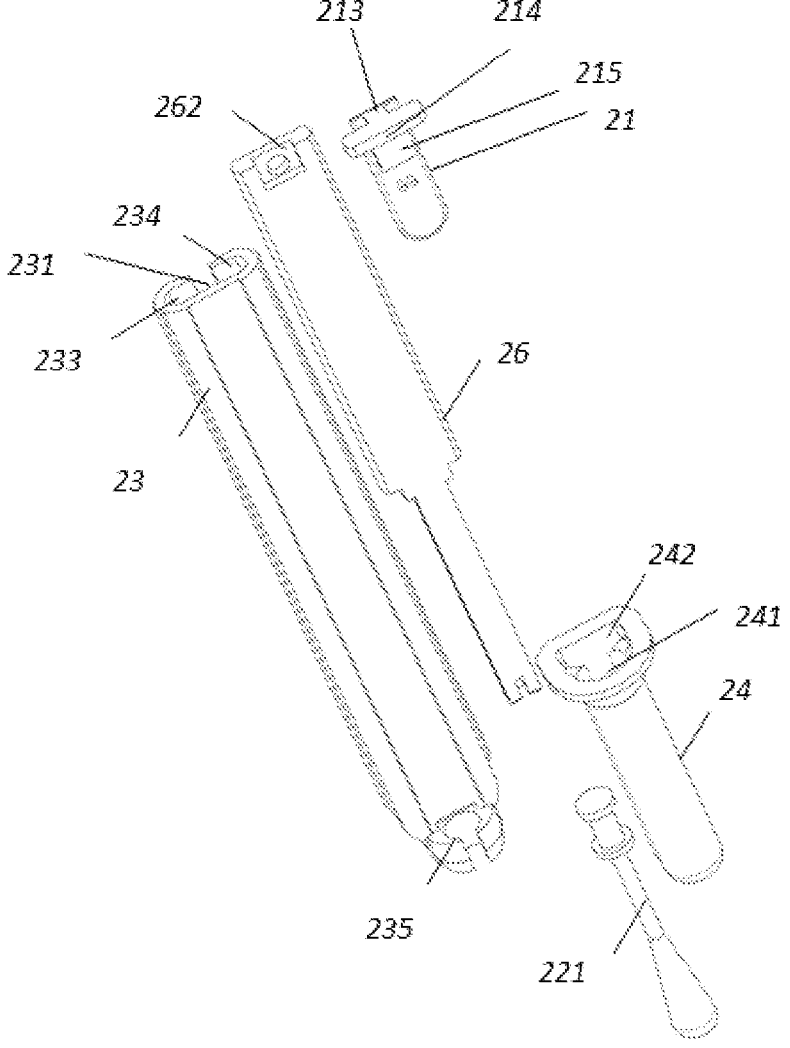
FIG. 9 is a schematic diagram showing a disassembled structure of a test device in a detailed embodiment of the present invention.

A detachable combination means that the connection relationship of two parts is in several different states or locations, for example, when two physical parts are separated initially, they can connect or combine together at an appropriate first condition; and at an appropriate second condition, the two parts can be separated, and the separation is a separation of physical space, without contact. Or, the two parts are combined together initially, and when appropriate, the two parts can be separated physically, or two objects are separated initially, and when required, they combine together to complete some functions, and then separate, or combine again for some purposes subsequently. In a word, the combination or separation of two parts is easy, and such combination or separation can be repeated for many times, of course, it can be one-time combination or separation. In addition, the combination may be a detachable combination between two parts, or a mutually detachable combination between three or more parts, for example, with three parts, the first part is detachably combined with the second part, and the second part can also be detachably combined with the third part, and the first part can also be detachably combined with or separated from the third part. Moreover, the combination between them can be achieved by two detachable objects or indirectly through another object. Here, the absorbing element 201 can be detachably combined with the chamber 13 for accommodating the testing element 18. The detachable combination can be in a direct or an indirect way, as described in details below. The carrier 16 with a testing element is also detachably combined with the chamber 13 of a holding element 18, such that they are combined to form a test device, but after disassembly, they may each have their own purposes. In the present invention, after the absorbing element 201 is separated from the testing element, the absorbing element can be separately sterilized, such as sterilization by high temperature, X-ray, radiation, etc. After the sterilization, the absorbing element is combined with the testing element. By this way, the absorbing element can be brought into fluidic communication with the testing element such that the liquid from the absorbing element can flow from the absorbing element to the testing element. In some embodiments, the absorbing element 201 is fixedly disposed on the chamber 13 that accommodates the testing element, for example, on an end (as shown in FIG. 9); at this time, the testing element is not assembled on the chamber 13: after sterilization, the testing element 18 or the carrier 16 with the testing element is inserted into the chamber 13, and then fixed on the chamber 13 by a locking structure.

Testing Element

The "testing element" used herein refers to an element that can be used to detect whether a sample or a sample contains an interested analyte. Such testing can be based on any technical principles, such as immunology, chemistry, electricity, optics, molecular science, nucleic acids, physics, etc. The testing element can be a lateral flow test strip that can detect a variety of analytes. Of course, other suitable testing elements can also be used in the present invention.

Various testing elements can be combined for use in the present invention. One form of the testing elements is test paper or transverse-flow test paper. The test papers used for analyzing the analyte (such as drugs or metabolites that show physical conditions) in samples can be of various forms such as immunoassay or chemical analysis. The analysis mode of non-competition law or competition law can be adopted for test papers. A test paper generally contains a water absorbent material that has a sample application area, a reagent area and a testing area. Fluid or liquid samples are added to the sample application area and flow to the reagent area through capillary action. If analyte exists in the reagent area, samples will bind to the reagent. Then, samples continue to flow to the testing area. Other reagents such as molecules that specifically bind to analyte are fixed in the testing area. These reagents react with the analyte (if any) in the sample and bind to the analyte in this area, or bind to a reagent in the reagent area. Marker used to display the detection signal exists in the reagent area or the detached mark area.

Typical non-competition law analysis mode: if a sample contains analyte, a signal will be generated; and if not, no signal will be generated. Competition law: if no analyte exists in the sample, a signal will be generated; and if analyte exists, no signal will be generated.

The testing element can be a test paper, which can be water absorbent or non-absorbing materials. The test paper can contain several materials used for delivery of liquid samples. One material can cover the other material. For example, the filter paper covers the nitrocellulose membrane. One area of the test paper can be of one or more materials, and the other area uses one or more other different materials. The test paper can stick to a certain support or on a hard surface for improving the strength of holding the test paper.

Analyte is detected through the signal generating system. For example, one or more enzymes that specifically react with this analyte is or are used, and the above method of fixing the specifically bound substance on the test paper is used to fix the combination of one or more signal generating systems in the analyte testing area of the test paper. The substance that generates a signal can be in the sample application area, the reagent area or the testing area, or on the whole test paper, and one or more materials of the test paper can be filled with this substance. The solution containing a signifier is added onto the surface of the test paper, or one or more materials of the test paper is or are immersed in a signifier-containing solution, and the test paper containing the signifier solution is made dry.

Each area of the test paper can be arranged in the following way: sample application area, reagent area, testing area, control area, area determining whether the sample is adulterated, and liquid sample absorbing area. The control area is located behind the testing area. All areas can be arranged on a test paper that is only made of one material. Also, different areas may be made of different materials. Each area can directly contact the liquid sample, or different areas are arranged according to the flow direction of liquid sample; and a tail end of each area is connected and overlapped with the front end of the other area. Materials used can be those with good water absorption such as filter papers, glass fibers or nitrocellulose membranes. The test paper can also be in the other forms.

The nitrocellulose membrane test strip is commonly used, that is, the testing area includes a nitrocellulose membrane (NC) on which a specific binding molecule is fixed to display the detecting result; and other test strips such as cellulose acetate membrane or nylon membrane test strips can also be used. For example, the test strips and similar apparatuses with test strips disclosed in the following patents can be applied to the testing elements or detection devices in this invention for analyte detection, such as the detection of the analyte in the samples; U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620, and 6,403,383. The test strips and similar device provided with a test strip disclosed in the above patent literatures may be applied in the testing element or detecting apparatus of the present invention for the detection of an analyte, for example, the detection of an analyte in a sample.

The test strips used in the present invention may be those what we commonly called lateral flow test strip, whose specific structure and detection principle are well known by those with ordinary skill in the art. Common test strip 18 (FIG. 1) includes a sample collecting area or a sample application area 183, a labeled area (182), a testing area 181 and a water absorbing area 184; the sample collecting area includes a sample receiving pad, the labeled area includes a labeled pad, the water absorbing area may include a water absorbing pad: where the testing area includes necessary chemical substances for detecting the presence or absence of analyte, such as immunoreagents or enzyme chemical reagents. The nitrocellulose membrane test strip is commonly used, that is, the testing area 181 includes a nitrocellulose membrane, and an area 1811 on which specific binding molecule is fixed to display the detecting result; and other test strips such as cellulose acetate membrane or nylon membrane test strips can also be used. Of course, in the downstream of the testing area, there may also be a detecting result control area 1812: generally, test strips appear on the control area and the testing area in the form of a horizontal line, that is a detection line or a control line, and such test strips are conventional. Of course, they can also be other types of test strips using capillary action for detection. In addition, there are often dry chemical reagent components on the test strip, for example immobilized antibody or other reagents. When the test strip meets liquid, the liquid flows along the test strip with the capillary action, and the dry reagent components are dissolved in the liquid, then the liquid flows to the next area, the dry reagents are treated and reacted for necessary detection. The liquid flow mainly relies on the capillary action. Here, all of them can be applied to the test device of the present invention or can be disposed in contact with the liquid samples in the detection chamber or used to detect the presence or absence of analyte in the liquid samples that enter the detection chamber, or the quantity thereof.

In addition to the foregoing test strip or lateral flow test strip which is used to contact with the liquid to test whether the liquid samples contain analytes. The testing element of the present invention may be used as a test device by itself to detect an analyte in a sample. Therefore, the test device here is equal to a testing element. For example, after being mixed with the treatment solution, the fluid sample is detected with a testing element directly, when the receiving device is described to treat a fluid sample, the testing element may be used for detection alone.

Analyte

Examples that can use the analyte related to this invention include small-molecule substance, including drugs (such as drug abuse). "Drug of Abuse" (DOA) refers to using a drug (playing a role of paralyzing the nerves usually) not directed to a medical purpose. Abuse of these drugs will lead to physical and mental damage, produce dependency, addiction and/or death. Examples of DOA include cocaine, amphetamine AMP (for example, Black Beauty, white amphetamine table, dextroamphetamine, dextroamphetamine tablet, and Beans); methylamphetamine MET (crank, methamphetamine, crystal, speed); barbiturate BAR (e.g., Valium, Roche Pharmaceuticals, Nutley, and New Jersey); sedative (namely, sleep adjuvants); lysergic acid diethylamide (LSD); depressor (downers, goofballs, barbs, blue devils, yellow jackets, methaqualone), tricyclic antidepressants (TCA, namely, imipramine, Amitryptyline and Doxepin); methylene dioxymetham-phetamine (MDMA); phencyclidine (PCP); tetrahydrocannabinol (THC, pot, dope, hash, weed, and the like). Opiates (namely, morphine MOP or, opium, cocaine COC: heroin, oxycodone hydrochloride); antianxietics and sedative hypnotics, antianxietics are drugs for alleviating anxiety, tension, fear, stabilizing emotion and having hypnosis and sedation, including benzodiazepines (BZO), non-typical BZs, fusion dinitrogen NB23Cs, benzoazepines, ligands of a BZ receptor, open-loop BZs, diphenylmethane derivatives, piperazine carboxylates, piperidine carboxylates, quinazoline ketones, thiazine and thiazole derivatives, other heterocyclic, imidazole sedatives/analgesics (e.g., oxycodone hydrochloride OXY, metadon MTD), propylene glycol derivatives, mephenesin carbamates, aliphatic compounds, anthracene derivatives, and the like. The test device of the present invention may be also used for detecting drugs which belong to medical use but is easy to be taken excessively, such as tricyclic antidepressants (Imipramine or analogues), acetaminophen and the like. These medicines will be resolved into micromolecular substances after being absorbed by human body, and these micromolecular substances will exist in blood, urine, saliva, sweat and other body fluids or in some of the body fluids.

For example, the analyte detected by the present invention includes but not limited to creatinine, bilirubin, nitrite, proteins (nonspecific), hormones (for example, human chorionic gonadotropin, progesterone, follicle-stimulating hormone, etc.), blood, leucocyte, sugar, heavy metals or toxins, bacterial substances (such as, proteins or carbohydrates against specific bacteria, for example, *Escherichia coli.* 0157:H7, *Staphylococcus, Salmonella, Fusiformis* genus, *Camyplobacter* genus, *L. monocytogenes, Vibrio*, or *Bacillus cereus*) and substances associated with physiological features in a urine sample, such as, pH and specific gravity. The chemical analysis of any other clinical urine may be conducted by means of a lateral cross-flow detection way and in combination with the device of the present invention. In some embodiments, the treatment solution contained in the receiving device is free of an analyte.

Test Device

The test device refers to an apparatus for detecting the presence or absence of an analyte. The collection device refers to a part that receives a part of the test device or a part that the test device inserted into the receiving device to mix or process the samples, elute the absorbing element 201 and treat the liquid or liquid samples. The receiving device is not present especially for receiving the test device, and may be present alone, and independently has the function of treating a fluid sample. The test device may include a testing element having a test function, for example, a carrier with a testing element, or may also include an accommodating element of a carrier, for example, a chamber 13 for accommodating the testing element. The test device may include an absorbing element 201 for collecting a sample, or include an absorbing element (a collector) with a connecting rod. The absorbing element 2022 with collected samples may be also called a collection device or a collector. The collection device may also include a test device: or the collector may be detachably combined with the test device. The collection device is assembled with the collection device in detection to complete the test. The test device may also include a collecting device. It is also possible that the collection device and the test device are an integrated structure, and once liquid samples are collected, the detection can be performed immediately to obtain the test result. Here, the connotation of the test device or testing element is interchangeable.

The "receiving device" here is merely for the convenience of description. In a detailed embodiment, the receiving device 14 receives a portion of the collector, for example, receives an absorbing element 2022, or receives a portion of the test device with an absorbing element. When the receiving device is not for the purpose of receiving, it may be called a sample treatment/sample mixing device. In the process of treating a sample, the test device may be not received, but the absorbing element may be only received to achieve independent completion (detailed description is as follows). To sum up, the "receive" here neither defines the scope of the device, nor play the defining role of claims of any Patent Law, but is merely a way of expression for the convenience of description.

In some detailed embodiments, the test device of the present invention includes a chamber 13 for accommodating the testing element; the testing element 18 has a first position and a second position in the chamber. When the testing element is located in the first position, the testing element is locked on or in the chamber 13. In some preferred embodiments, the test device includes a movable element 11; the movable element has a first position and a second position in the chamber 13, capable of moving to the second position from the first position. In some embodiments, when the movable element is located in the first position, the movable element is located in the locking position or locking state with the chamber 13: when or after being unlocked, the movable element may move to the second position from the first position. In some embodiments, the testing element 11 may drive the testing element to move from the first position to the second position.

Figures 16, 17:
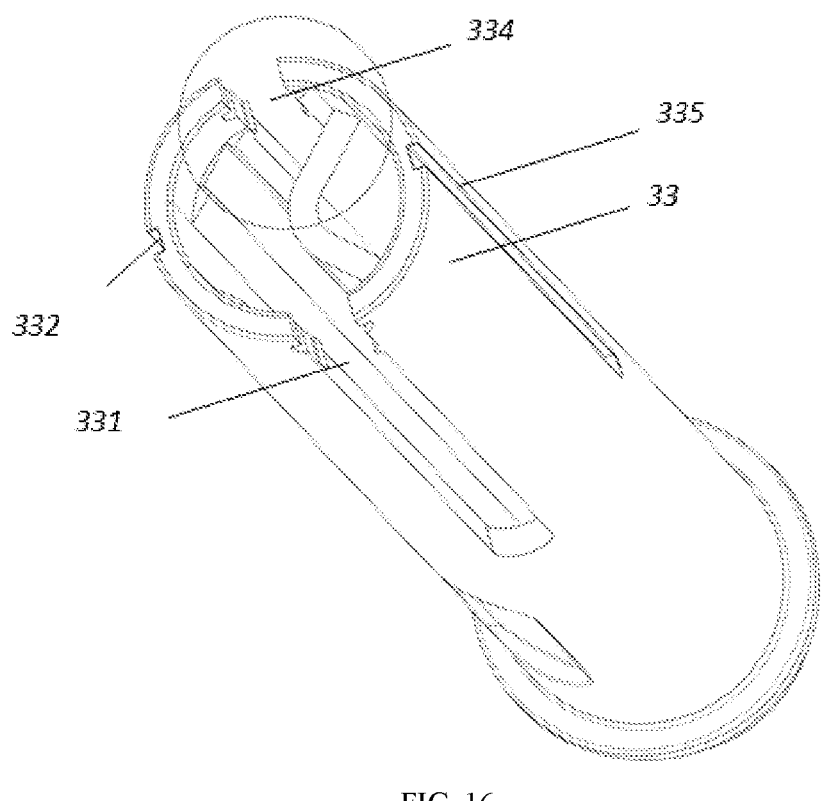
FIG. 16 is a schematic diagram showing a three-dimensional structure of the chamber.
FIG. 17 is an enlarged schematic diagram showing an upper structure A of the chamber.

In some embodiments, the chamber for receiving the testing element has a three-dimensional structure as shown in FIGS. 1-9. The chamber is used for receiving the testing element or bearing the carrier of the testing element. The carrier and chamber are in a locking state when in the first position, and may move to the second position from the first position when unlocked. In some embodiments, when the chamber is in the second position, a portion of the testing element contacts with a liquid sample to initiate the detection. In some embodiments, in case of being in the first position, the testing element is located in the chamber without exposure; in case of being in the second position, the testing element or a portion thereof stretches out of the chamber (FIG. 17), and the portion of the testing element stretching out of the chamber 13 contacts with the liquid sample. In some embodiments, the liquid sample is located in a chamber for treating liquid samples (a treatment chamber 15), for example, as shown in FIGS. 5A-D. The treatment chamber 15 contains a liquid sample; after the chamber 13 for accommodating the testing element is inserted into the treatment chamber 151, the testing element or the carrier bearing the testing element is unlocked from the locking state of the first position, thus moving from the first position to the second position. A portion of the testing element stretches into the treatment chamber 15 to contact with the liquid sample, thus completing the adsorption on the liquid sample.

It is understood that the testing element 18 or the carrier 16 bearing the testing element is located in two states or two position states in the chamber 13. In some embodiments, the chamber 13 is cylindrical, or just like a three-dimensional cuboid as shown in FIG. 1; one end 103 is opened and another end 1032 is also opened; another end 1032 thereof has a structure which may be detachably assembled with the collector 201. The structure 156 may be an insertion hole 191; one end 2023 of the collector 201 may be inserted into the insertion hole 191, or fixed with the chamber 13 in a threaded manner, thus being assembled into a collector. The collector has a rod-like body 2024 and an absorbing element 2022. In some embodiments, the locking state of the testing element or carrier or movable element with the chamber is fixed on the chamber via a locking mechanism. The locking structure has locking and unlocking states; in case of being in the locking state, the position fixed on the chamber 13 may be fixed or not easy to move; in case of being in the unlocking state, the element fixed on the chamber may move or slide on the chamber. In some embodiments, the chamber includes a portion of locking structure, used for locking the testing element 18 or carrier 16 such that the testing element or carrier is in a locking state relative to the chamber 13.

Figure 4:
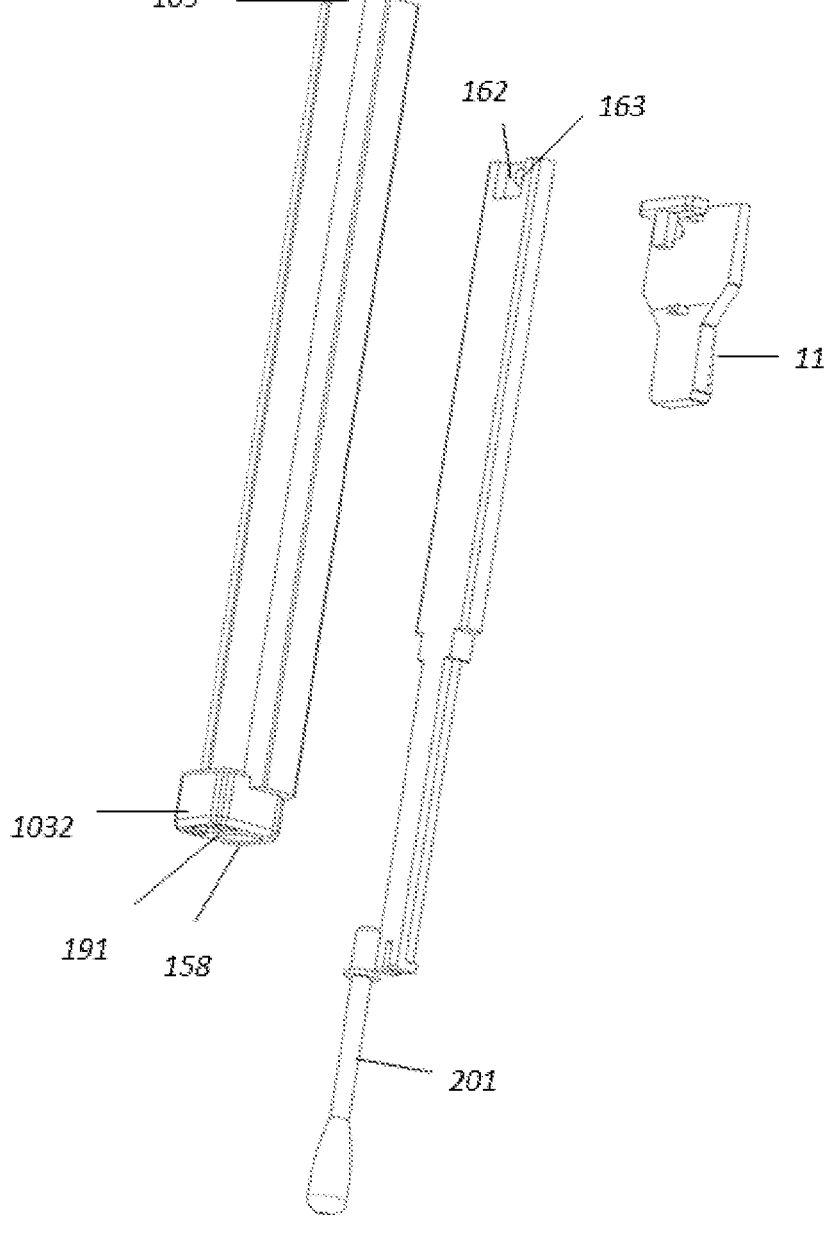
FIG. 4 is a schematic diagram showing a portion of disassembled structure in a detailed embodiment of the present invention.
Figure 5A:
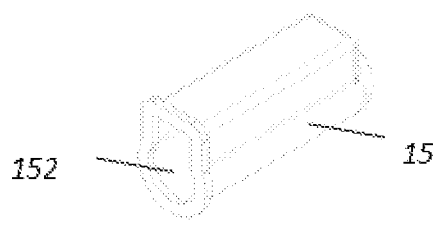
FIG. 5A is a structure diagram showing an accommodating container or accommodating device in a detailed embodiment of the present invention.
Figures 5B, 5C, 5D:
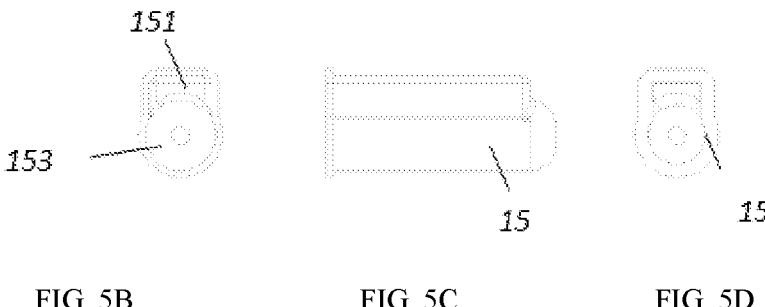
FIG. 5B is an upward view of the accommodating device.
FIG. 5C is a left view.
FIG. 5D is a top view of the accommodating device.
Figures 6, 7:
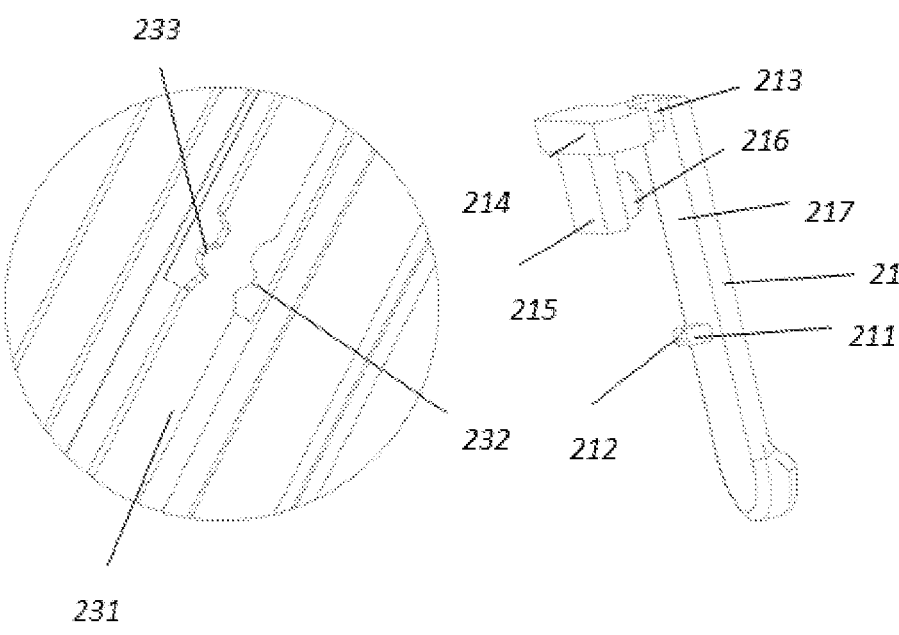
FIG. 6 is an enlarged schematic diagram showing a portion of a locking structure in a detailed embodiment of the present invention.
FIG. 7 is an enlarged structure diagram showing a movable element in a detailed embodiment of the present invention.
Figure 8:
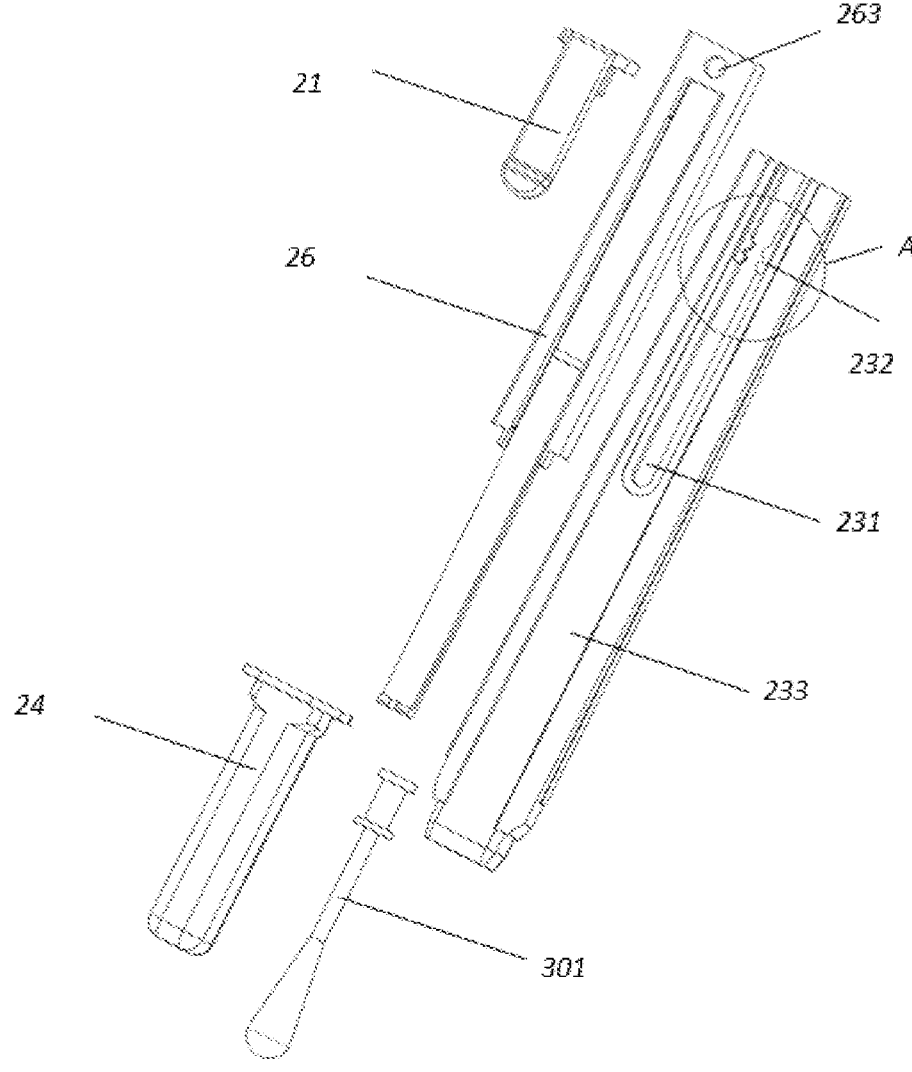
FIG. 8 is a schematic diagram showing a disassembled structure of a test device in a detailed embodiment of the present invention.

A portion of the locking structure is shown in FIGS. 2 and 3; or, as shown in FIGS. 6-7, the portion of the locking structure includes grooves 133,134 which are disposed on the sliding groove of the chamber and matched with the bolts or cylinders 111,112 on the movable element 11. When the movable element is matched with the grooves to form a locking state, the sliding rail 113 on the movable element is located in the sliding groove of the chamber 13. The groove structures herein partially protrude relative to the edge of the sliding groove such that the movable element is located in a more stable position in the sliding groove to achieve more firm fixation. Certainly, channels 135,136 which enable the bolts to access into the grooves readily and channels which enable the bolts to be separated from the grooves are disposed at both sides of the grooves on the sliding groove. In this way, the bolts readily enter into the grooves to be in a locking state, and are relatively readily separated from the grooves to be in an unlocking state. The movable element, e.g., a sheet structure covers on the surface of the sliding groove; the sheet structure has two faces, one face 118 is facing the sliding groove, and another face 119 is facing the operator; the face facing the sliding groove is provided with bolts 111,113, and the sliding groove 113 is also configured. One end of the chamber 13 having an opening 103 has two faces, one is provided with a sliding groove 131, and the sliding groove is generally disposed in a middle position of a face of the chamber. In this way, the face of the chamber is divided into two portions by the sliding groove. A positioning piece is disposed on the sliding rail of the movable element; the positioning piece is connected with the sliding groove in a shape of "T", and the positioning piece located at both sides of the sliding rail 113 is matched with the opening 103 at one end of the opening of the chamber. In some embodiments, as shown in FIG. 4, the positioning piece is connected with the insertion piece 115; the insertion piece is matched with the receiving opening 162 (as shown in FIG. 4) such that the movable element 11 is connected and fixed with the carrier 16. To achieve more firm connection, the insertion piece 115 is further provided with a bolt 116; the bolt is matched with the insertion hole 163 on the carrier such that the carrier is connected with the movable element. The carrier is inserted into the chamber 13 via the opening 103 at one end of the chamber during assembly. Both ends of the positioning piece 114 are in contact with the inner walls 140,141 of the chamber, and the sliding rail 113 is located in the sliding groove on the chamber 13. At this time, two bolts on the movable element are received by the notch on the sliding groove and matched with each other to be a fixed or locked state.

The movable element is pushed downward once again in need of being unlocked such that the bolts 111,112 are separated from the notches 133,134 on the sliding groove. At this time, both sides of the positioning piece 114 are still in contact with the inner walls 140,141 of the chamber. Such a contact avoids the position change of the movable element, and the sliding rail 113 slides in the sliding groove 131, thus driving the carrier 16 to move in the chamber 13 such that a portion of the carrier stretches out of the wall body from the original first position of being fully in the chamber.

In some embodiments, for example, in another detailed embodiment as shown in FIGS. 6-9, the test device includes a chamber 23 for receiving the carrier; the chamber includes a structure 235 whose one end has an opening and has a sliding groove 231 and another end has a fixed collector; the chamber is flat: both sides of the sliding groove 231 have inner walls 233 and 234. The inner walls are matched with a horizontal positioning piece 214 on the movable element; the sliding rail 213 on the movable element is horizontally inserted into the sliding groove. Similarly, the movable element has an insertion piece 215 used for inserting into the receiving opening 263 in the carrier such that the carrier is connected with the movable element. The carrier has a testing element; the water absorbing area of the testing element is located at one end of the receiving opening 263; and the sample application area of the testing element is located at a relative end of the carrier.

Similarly, as shown in FIG. 6-7, a portion of the locking structure is disposed on the sliding groove. As shown in FIG. 6, the sliding groove has two protruding structures which are facing to each other relatively; the protruding structures have notches; the middle distance between the two protruding structures is less than the width of the sliding groove. When the two bolts 212,211 on the movable element are respectively received by the notches, the movable element is in the locking position by means of mechanical force; when the bolts are separated, the movable element is in a slidable position such that the movable element moves to the second position from the first position by means of the sliding of the operator; the distance of the sliding groove defines the furthest moving distance of the movable element.

Carrier Element

Figure 10:
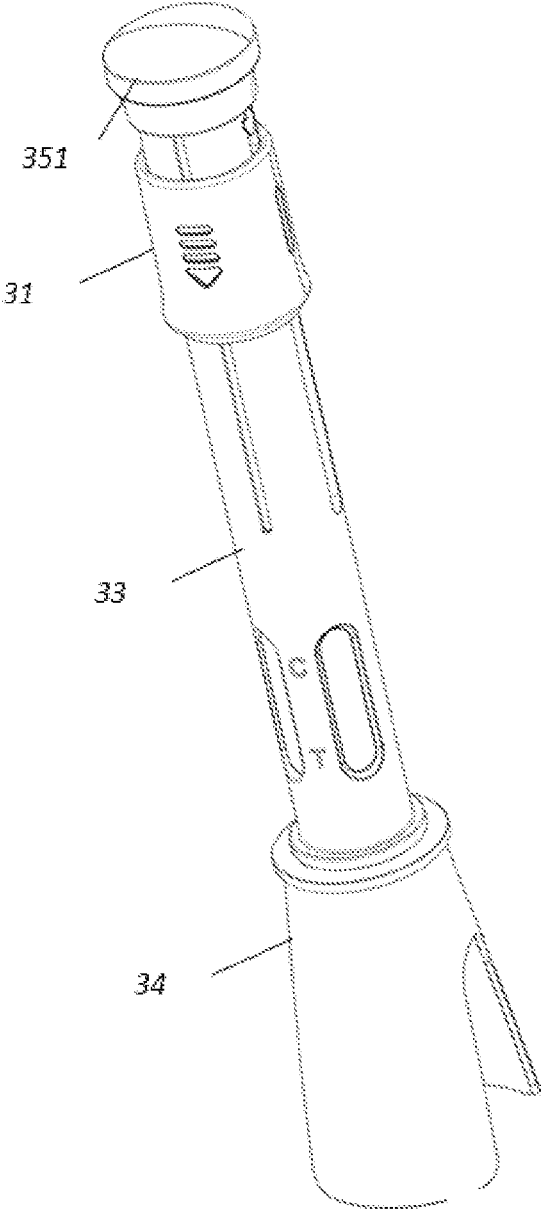
FIG. 10 is a schematic diagram showing an assembled three-dimensional structure of a test device in another detailed embodiment of the present invention.
Figure 11:
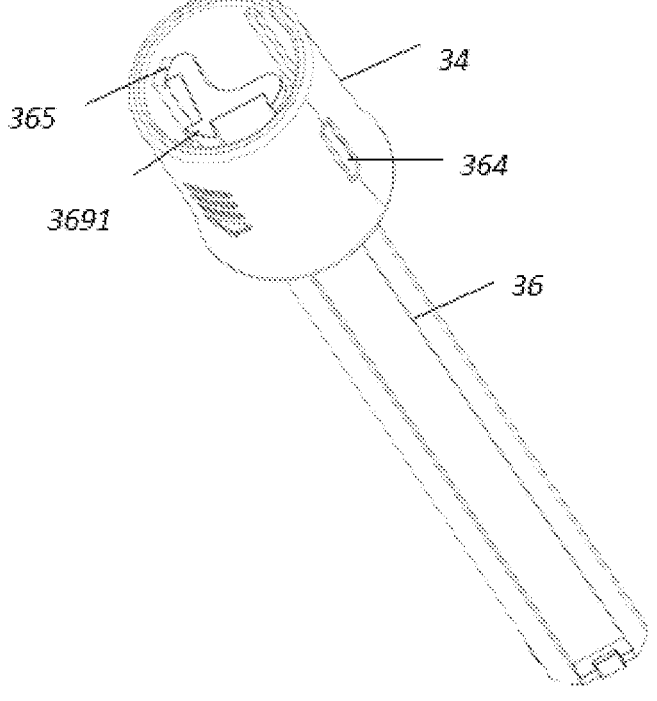
FIG. 11 is a schematic diagram showing a three-dimensional structure assembled by a movable element and a carrier.

In some detailed embodiments, the testing element may be also disposed on some carrier elements; then the carrier elements contain the testing element to complete the detection and assay of the analytes in fluid samples. Therefore, in some embodiments, the test device includes a carrier 16, and the carrier is provided with a testing element 18. In some embodiments, the carrier is located in the chamber 13 for accommodating the testing element, and the carrier 16 has a first locking position and a second position in the chamber; and the second position is not a locking state. As shown in FIGS. 9-11, for example, on some carrier 16, generally, a carrier has one or more grooves 161; the testing element 18 is located in the groove 161, and the carrier generally has a front and a back 164, and the testing element 18 is located on the front of the carrier, or located in the front groove 161. The number of grooves is not limited: generally, a testing element is located in a groove; usually, a testing element may be used to detect an analyte in samples. Of course, a testing element may be used to simultaneously detect one or more, a or a plurality of analytes.

In some detailed embodiments, the carrier 16 includes two parts, and one of them is a groove structure 161; the groove structure is used for holding a testing element: generally, the groove structure is used for holding the testing area or labeled area of the testing element such that the testing area or the labeled area is located in a relatively fixed and safe position. Such a design may ensure the accuracy and reliability of the test results. The carrier further includes an area connected to the movable element 11. The structure of the area is designed in fixed fit with the movable element.

The connecting area is located on one end of the carrier, as shown in FIG. 1, one end of the carrier 16 has an insertion opening 162; the insertion opening is used for receiving the insertion of the insertion piece 115 on the movable element 11, thus achieving the connection between the movable element and the carrier. Certainly, such a connection mode may be any other mode, for example, buckle, bolt and socket and the like are available. To achieve more firm connection between the carrier 16 and the movable element 11, a bolt 116 is disposed on the insertion piece 115 of the movable element 11; the bolt stretches from the insertion piece to the face back 117 to the insertion piece: an insertion hole 163 is disposed on the insertion opening 162 of the carrier. In this way, when the insertion piece 115 on the movable element is inserted into the insertion opening 162 of the carrier, the bolt 116 on the insertion piece 115 is inserted into the insertion hole 163 on the carrier, thus achieving the fixed connection between the carrier and the movable element. It should be understood that after the bolt 116 is inserted into the insertion hole 163 on the carrier, there is a certain distance between the front (one face with a test stripe) of the carrier and the back face 117 of the movable element. The distance is defined by the length of the sliding rail 113. In this way, when the carrier 16 is inserted into the chamber from one end 103 of the chamber 13, the sliding rail 113 is located in the sliding groove 131; the movable element covers on the outer surface of the chamber 13, and the carrier is located in the chamber 13. Transverse members 114 distributed at both sides of the sliding rail 113 on the movable element 11 cover on the opening at one end of the chamber 13, which seems that the carrier is blocked in the chamber from the shape. Based on the above description, the carrier enters to the chamber, and is located in the locking position: unlocking is performed in need of moving downward, thus achieving the movement from the first locking position to the second position. When the movable element moves on the sliding groove, the transverse positioning piece 114 slides from the first position to the second position by means of the inner walls 140,141 at both sides of the sliding groove 131 in the chamber 13.

In some embodiments, samples are collected with a collector 201 firstly, for example, fluid samples, such as saliva, sputum, urine and nasal secretion; and the analyte comprises coronavirus. The collector 201 is fixedly connected with the another end 1032 of the chamber 13 in the test device. In this way, after collection, the collector is inserted into the receiving device 15: a treatment fluid is loaded in the receiving device in advance. The collector is inserted into the chamber 152 of the receiving device 15 to contact with the treatment fluid such that the sample in the collector is dissolved into the treatment fluid: if it is virus, the sample is lysed by the treatment fluid: if not, the sample is eluted or dissolved. At this time, the carrier moves to the second position from the first locking position of being fully accommodated by the chamber by means of the sliding of the movable element. A portion of the carrier stretches out of the chamber 13, and enters to the chamber of the receiving device 15 to contact with the liquid; the testing element on the carrier contacts with liquid; and the liquid flows to the labeled area, testing area and the water absorbing area successively from the sample application area of the testing element relying on capillary force, thus completing the assay of an analyte in the sample.

In some embodiments, the receiving device includes two spaced chambers: one is used for inserting the collector, and another chamber 153 is used for inserting a portion of the carrier. In this way, a partition is disposed in the two chambers of the accommodating device, and the bottom is in liquid communication, similar to the theory of a communicating vessel. By such a design mode, when the collector is inserted into the chamber 153, the side wall of the portion of the chamber is desired to be soft, and the side wall of the chamber may be pressed by hands such that the collector is pressed to accelerate the sample dissolving or lysis. When the carrier is required to get into the chamber 153, the collector is neither desired to disturb the insertion of the carrier, nor desired to contact the testing element directly. Generally, the testing element is soft, and desired to be fixed in the position of the carrier, if the testing element changes in position during operation, it affects the test effect. Therefore, a partition is disposed between the chamber 152 where the carrier is inserted and the chamber 152 where the collector is inserted to be spaced, thus avoiding mutual influence. For another example, the accommodating device 24 as shown in FIG. 9 includes two different shapes of chambers, one is a chamber 241 similar to a collecting chamber and roughly cylindrical, and another chamber 242 is a regular cube, similar to the structure and shape of the carrier. In this way, even though there is no partition, it is also free of mutual effect or disturbance in the operation of the collector and the testing element on the carrier.

In some embodiments, for example, in some other embodiments as shown in FIG. 10-15, when the chamber 33 for accommodating the testing element is round, the carrier 36 is designed in a curved surface. Therefore, the groove for accommodating the testing element on the carrier is distributed according to a curved surface. Specifically, the carrier shows a regular curved surface on the whole. The middle part of the curved surface has a ridge 3691; the carrier is divided into two parts by the ridge 3691; each part is provided with a groove for accommodating a reagent strip; the testing element is located in the groove 161. The ridge is provided with horizontal extension areas 3612 to penetrate the grooves of the whole carrier; the extension areas are distributed above the grooves on the ridge. In this way, when the testing element 18 is disposed in the grooves, the extension areas may protect the test stripe from being damaged. The major reason is that the carrier 36 is driven to move in the chamber 33: during the moving process, it needs to ensure the testing element free of damage, and also needs to ensure a fixed position of the testing element in the groove. Otherwise, the location change of the testing element will also affect the accuracy of the final test result. For example, household operation has high arbitrariness because the operator does not possess enough professional knowledge, which demands for the fixed position of each component and for the convenience of the operation.

Figure 12:
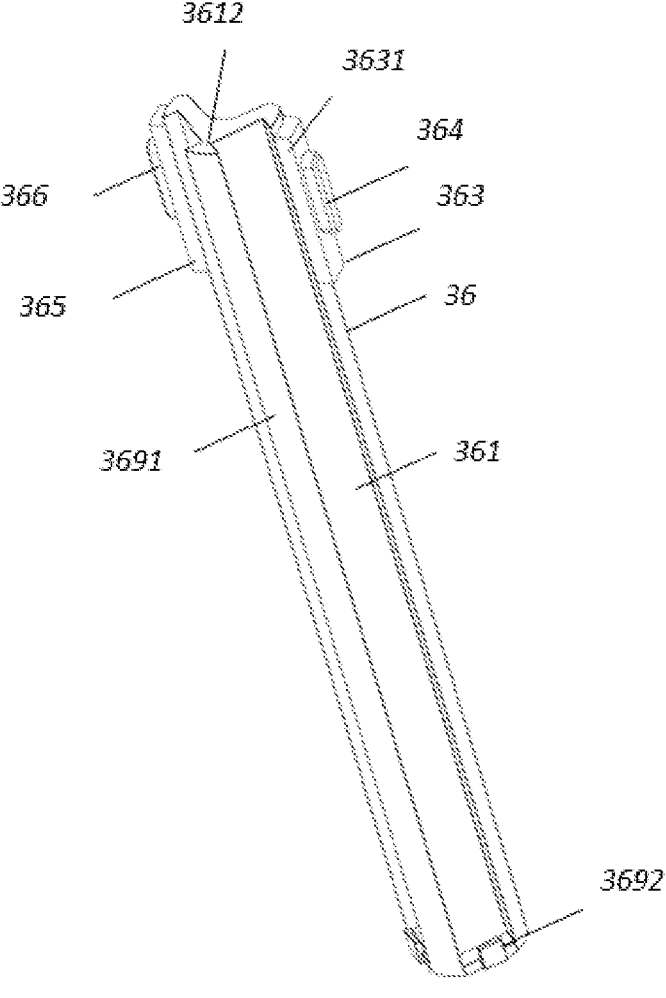
FIG. 12 is a schematic diagram showing a three-dimensional structure of the carrier.
Figure 13:
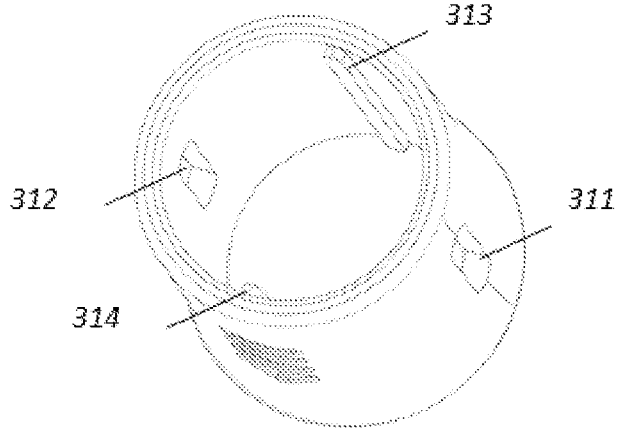
FIG. 13 is a schematic diagram showing a three-dimensional structure of the movable element.

Moreover, to keep the position of the testing element in the groove still and not separated from the groove, a tail end of the carrier is provided with a blocking piece 3692 (FIG. 12). The blocking piece has a plane in contact with the tail end of the testing element (not shown), thus preventing the test stripe from falling off from the groove. In the subsequent movement, the carrier needs to stretch out of the chamber 33, and the stretched portion needs to be immersed into liquid. The testing element is not desired to slip out of the groove. In some other examples, through holes are opened in the grooves and distributed in the different positions of the grooves. It needs to be indicated that one of the through hole is disposed on the plane of a stopper to be communicated with the plane. When the tail end of the testing element touches the surface of the stopper, a portion of testing element is exposed through the through hole, in particular to the sample application area of the partial testing element is exposed. In this way, when the carrier stretches out of the chamber 33 and enters to the chamber of a collection device, the carrier will directly touch the liquid sample in the chamber of the collection device; the sample contacts with the sample application area of the testing element after passing through the through hole. Another through hole is disposed in a roughly middle position of the groove to prevent the liquid sample from wetting the test stripe in advance after passing through the capillary gap formed between the back of the testing element and bottom surface of the groove, thus affecting the normal reaction. The through hole plays the role of blocking. Generally, the liquid flow rate by the capillary force of the test stripe is much slower than the liquid flow rate of the capillary gap. In this way, if other areas of the testing element are moistened in advance, for example, a testing area, the may not be completed when the liquid sample carrying analyte flows to the testing area. Because the testing area is moistened by the liquid in advance, the area is free of capillary force, thus affecting the flow of the liquid sample.

In some embodiments, a structure fixed with the movable element 31 is disposed on another end of the carrier, namely, one end close to the water absorbing area 184 of the testing element. The carrier is connected with the movable element by the structure. In this way, the movable element moves to drive the carrier to move. The carrier may not only drive the testing element to move, but also protect the testing element from being damaged. The fixed structure is a fixed piece 364 which is disposed at both sides of the carrier and located on the sliding rail 363: side faces 3631,3632 of the sliding rail 363 are matched with the side face of the sliding groove 331 penetrating the side wall on the receiving chamber 33 such that the carrier has a fixed position in the chamber by means of the frictional force generated by the contact between the face of the sliding rail 363 and the face of the sliding groove.

Figure 14:
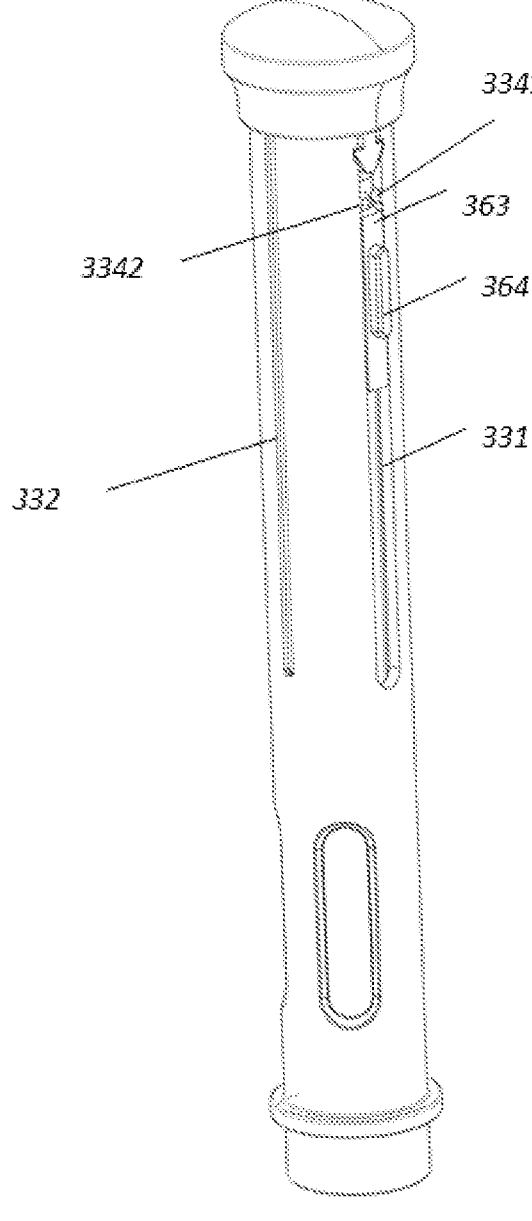
FIG. 14 shows a schematic diagram showing a three-dimensional structure assembled by a chamber and the carrier.
Figure 15:
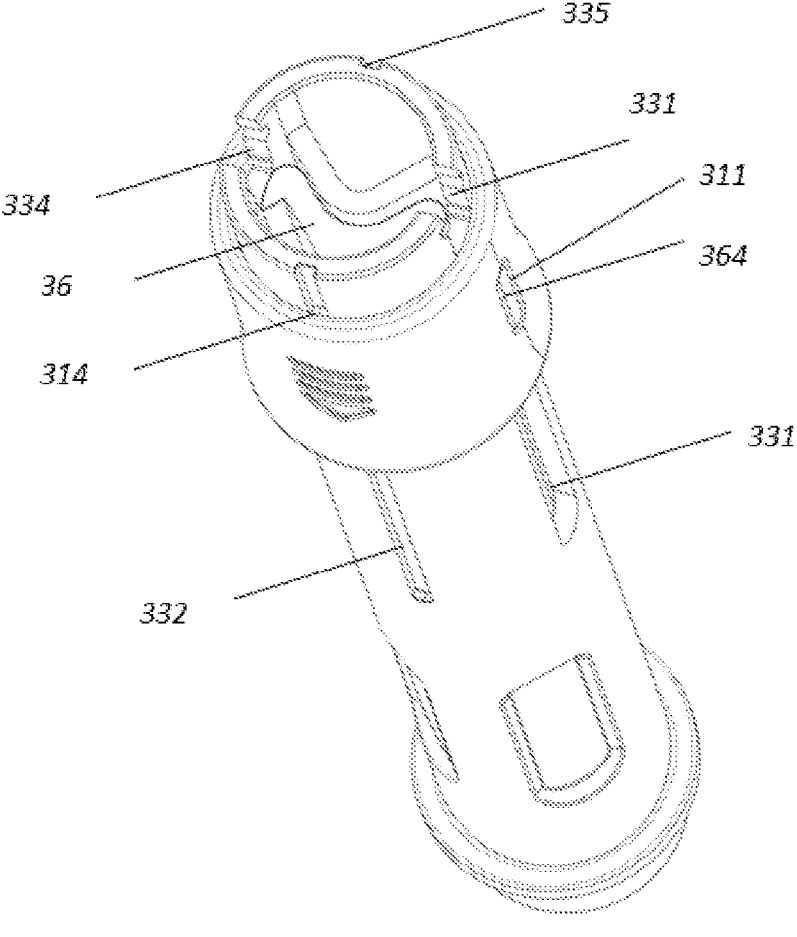
FIG. 15 is a schematic diagram showing a three-dimensional structure assembled by the chamber, the carrier and the movable element.

The fixed piece 364 located on the sliding rail is matched with the opening 311 of the movable element such that the carrier is fixedly connected with the movable element. The thickness and length of the fixed piece 364 are corresponding to the opening 311 on the movable element 31. In this way, the movable element with the carrier is assembled with the chamber 33 to form the test device. Specifically, as shown in FIG. 15, the movable element 31, e.g., a chamber, sliding rails 313,314 are distributed on the inner wall of the chamber; the sliding rails are symmetrically distributed: openings 311,312 are disposed on the accessories of the sliding rails 313,314 such that two openings are respectively combined with the fixed pieces 364,366 on the carrier. The sliding rail 314 on the inner wall of the movable chamber 31 is matched with the sliding groove 332 on the surface of the chamber 33; the sliding rail 313 is matched with the sliding groove 335 on another chamber 31. The sliding rail on the outer surface of the chamber has a depth and a sliding groove at the bottom instead of penetrating the side wall. Two sliding grooves 331,334 penetrating the side wall are disposed on the chamber; the sliding rail 363 on the carrier is disposed on the sliding groove 331. Because there is frictional force due to the contact between the face of the sliding groove and the side face of the sliding rail 363, the carrier will slide downward by means of gravity, as shown in FIG. 14. Specifically, the sliding groove on the chamber 33 has a certain length: some bulges 3341,3342 are disposed on one end of the sliding groove. The bulges are relatively protruding on the side wall of the sliding groove. When the sliding rail 363 on the carrier is located on the sliding groove, the bulges are located above the sliding rail 363 of the carrier to prevent the carrier from falling off from the sliding groove. When the carrier is inserted into the chamber, even though the sliding rail 363 will pass through the bulges on the sliding groove 331, the carrier may be inserted into the correct position due to the intrinsic elasticity of the plastic material. The sliding rails 363,366 on the carrier will be respectively clamped on the sliding grooves 331,334 once being in the correct position (as shown in FIG. 14). The carrier stays at the first fixed position by means of frictional force. The frictional force only overcomes the weight of the carrier available, and the weight of the movable element is also included. In an actual product, the total weight of the carrier, the test stripe and the movable element is about 20-50 g; therefore, it is available as long as the frictional force may have such a resistance. In operation, when the carrier needs to be moved, the carrier 36 is capable of moving in the chamber 33 only by slightly pushing the movable element 31 to move downward such that a portion of the carrier stretches into the accommodating device 34 to enable the testing element to contact the liquid.

The following specific technical solutions are a portion of the present invention.

1. A device for detecting an analyte in a sample, comprising a chamber for receiving a testing element, wherein the testing element has a first position and a second position in the chamber; the testing element is not in contact with a fluid sample when the testing element is located in the first position, and the testing element is in contact with a fluid sample when the testing element is located in the second position.

2. The device according to clause 1, wherein the chamber is further connected with a fluid sample collector, and the fluid sample collector is disposed on one end of the chamber.

3. The device according to any one of clauses 1-2, wherein the testing element and the chamber are in a locking state when the testing element is located in the second position.

4. The device according to any one of clauses 1-3, wherein a portion of the testing element stretches out of the chamber when the testing element is located in the second position.

5. The device according to any one of clauses 1-4, wherein the chamber further comprises a carrier used for bearing the testing element; the carrier has a first position and a second position in the chamber; and the carrier drives the testing element to change or move between the first position and the second position, alternatively, the carrier drives the testing element to move from the first position to the second position.

6. The device according to any one of clauses 1-5, wherein the carrier is connected to the chamber by a locking structure; the carrier dose not move with respect to the chamber when the carrier is in a locking first position, alternatively, the carrier is capable of moving to the second position from the first position relative to the chamber when the locking structure is unlocked.

7. The device according to any one of clauses 1-6, wherein when the carrier is located in the first position, the whole carrier is completely located in the chamber: when the carrier is located in the second position, a portion of the carrier stretches out of the chamber, thus contacting the liquid sample.

8. The device according to any one of clauses 1-7, wherein the device further comprises a movable element; the movable element is connected with the carrier; and the movable element is capable of moving the carrier from the first position to the second position.

9. The device according to any one of clauses 1-8, wherein the movable element comprises a first sliding rail and a second sliding rail; the carrier is fixedly connected with a second sliding rail.

10. The device according to any one of clauses 1-9, wherein the chamber comprises a first sliding groove coupled to the first sliding rail of the movable element and a second sliding groove coupled to the second sliding rail of the movable element; the second sliding groove is throughout a side wall of the chamber, and the first sliding groove is located on an outer surface of the chamber.

11. The device according to any one of clauses 1-10, wherein the movable element comprises a portion of the locking structure, and the chamber comprises another portion of the locking structure; the movable element is fixed on the chamber via the locking structure.

12. The device according to any one of clauses 1-11, wherein the carrier comprises a suspension structure, and the carrier is fixedly connected on the second sliding rail via the suspension structure.

13. The device according to any one of clauses 1-12, wherein the locking structure comprises a bulge structure and a notched structure; the movable element comprises the bulge structure; and an outer wall of the chamber comprises a notched structure.

14. The device according to any one of clauses 1-13, wherein the notched structure is located at a sheet structure on a side wall of the chamber; the sheet structure is a portion of the side wall of the chamber: meanwhile, the sheet structure is elastic.

15. The device according to any one of clauses 1-14, wherein the movable element is sleeved on an outer surface of the chamber, and the carrier and the second sliding rail are located in the chamber for receiving the testing element; the first sliding rail is located on the outer surface of the chamber and coupled to the first sliding groove on the surface of the chamber.

16. The device according to any one of clauses 1-15, wherein the chamber comprises a limiting structure; the limiting structure comprises an edge; the concave surface of the carrier is in contact with the edge of the limiting structure, wherein the carrier comprises a backbone structure.

17. The device according to any one of clauses 1-16, wherein the chamber for receiving the testing element comprises a first chamber side wall and a second chamber side wall, wherein the first chamber side wall is in front of the concave surface of the carrier, and the second chamber side wall is in front of the backbone structure.

18. The device according to any one of clauses 1-17, wherein the device further comprises an accommodating device; the accommodating device is used for holding the collector and a portion of the testing element.

19. The device according to any one of clauses 1-18, wherein the portion of the testing element comprises a partial sample application area.

20. The device according to any one of clauses 1-19, wherein the sample is one of saliva, sputum, urine and nasal secretion; and the analyte comprises coronavirus.

21. A method for detecting an analyte in a sample, wherein the method comprises steps of: providing a test device; and the device comprises a carrier for accommodating a testing element; the carrier is located in a chamber; the carrier is fixedly connected with a movable element on the chamber such that the movable element has a locked first position and a second position.

22. The method according to clause 21, wherein the movable element is fixed on the chamber via a locking structure.

23. The method according to clause 21, wherein the movable element is allowed to be unlocked, and then the movable element moves to the second position from the first position, thus driving the carrier to move from the first position to the second position.

24. The method according to clause 21, wherein the carrier is located in the chamber and not exposed when the movable element is located in the first position; the carrier is exposed outside the chamber and in contact with a liquid sample when the movable element is located in the second position.

25. The method according to clause 24, wherein providing an accommodating device, wherein the accommodating device is used for holding the collector; the collector is first inserted into the accommodating device, and then the movable element moves to the second position from the first position.

26. The method according to clause 24, wherein the collector is configured on the test device: a portion of the test device is allowed to get into an accommodating chamber and seal the accommodating while the collector is inserted into the accommodating device.

27. The method according to clause 23, wherein the movable element is coupled to a sliding rail via a sliding groove to move from the first position to the second position.

28. The method according to clause 27, wherein the sliding rail is configured on the chamber of the movable element; and the sliding groove is disposed on an outer wall of the chamber for holding the carrier.

29. The method according to clause 22, wherein the locking structure comprises a bulge structure located at the movable element and a notched structure located on the chamber and used for receiving a bulge.

30. The method according to clause 29, wherein when the movable element is located in a locking position, the bulge structure is located in the notched structure: when the movable element is located in an unlocking state, the bulge structure is separated from the notched structure.

31. A device for detecting an analyte in a sample, comprising a chamber for receiving a carrier element, wherein the testing element is located on the carrier element: the carrier has a first position and a second position in the chamber; the testing element is not in contact with a fluid sample when the testing element is located in the first position, and the testing element is in contact with a fluid sample when the testing element is located in the second position.

32. The device according to clause 31, wherein the chamber has a sliding groove, and comprises a sliding rail capable of sliding on the sliding groove, wherein the carrier is in the first position relying on frictional force between the sliding groove and the sliding rail.

33. The device according to clause 31, wherein the device further comprises a movable element capable of driving the carrier to move from the first position to the second position; the movable element is located on an outer surface of the chamber, wherein the movable element comprises an opening, and a fixing piece is disposed on the sliding rail of the carrier; the fixing piece is located in the opening such that the carrier is connected with the movable element.

34. The device according to clause 33, wherein the movable element is provided with a sliding rail; and the sliding rail is capable of moving out an outer wall of the chamber.

35. The apparatus according to clause 32, wherein the moving of the carrier from the first position to the second position is achieved by pushing the carrier to overcome frictional force.

All patents and publications mentioned in the description of the present invention are disclosures of the prior art and they may be used in the present invention. All patents and publications referred to herein are incorporated in the references as if each individual publication is specifically referred to separately. The invention described herein may be practiced in the absence of any one or more of the elements, any one limitation or more limitations that are not specifically recited herein. For example, the terms "comprising", "consisting of . . . substantively" and "consisting of . . . " in each example herein may be replaced by the rest 2 terms. The so-called "a/an" herein merely means "one", but does not exclude including 2 or more instead of including only one. The terms and expressions which have been employed herein are descriptive rather than restrictive, and there is no intention to suggest that these terms and expressions in this description exclude any equivalents, but it is to be understood that any appropriate changes or modifications can be made within the scope of the present invention and appended claims. It should be understood that, the embodiments described in the present invention are some preferred embodiments and features, and any person skilled in the art may make some changes and variations based on the essence of the description of the present invention, and these changes and variations are also considered to fall into the scope of the present invention and the independent claims and the appended claims.

The invention claimed is:

1. A device for detecting an analyte in a fluid sample, comprising:
   a chamber for receiving a testing element therein;
   a carrier located in the chamber, wherein the carrier is used for bearing the testing element;
   a movable element; and
   a locking structure;
   wherein the movable element is connected with the carrier; the movable element has a first locking position and a second position on the chamber,
   wherein, when the movable element is in the first position, the testing element on the carrier is not contact with the fluid sample; when the movable element is in the second position, the testing element is in contact with the fluid sample; after being unlocked, the movable element is capable of manually sliding to the second position from the first position, thus driving the carrier to move to the second position from the first position,
   wherein the chamber comprises a sliding groove, the movable element includes a sliding rail, and the movable element is capable of moving from the first position to the second position via the sliding rail sliding in the sliding groove of the chamber, wherein the movable element is connected with the chamber via the locking structure, and a portion of the locking structure is located on the sliding groove of the chamber, and another portion of the locking structure is located on the movable element, and wherein the portion of the locking structure located on the sliding groove comprises two opposing notches disposed relatively, and the portion of the locking structure located on the movable element comprises two bolts.

2. The device according to claim 1, wherein when the bolts are received by the notches, the movable element is locked in the first position; and when the bolts are separated from the notches, the movable element is capable of moving from the first position to the second position.

3. The device according to claim 2, wherein the carrier comprises a receiving opening; the movable element comprises an insertion piece; the insertion piece is inserted into the receiving opening, thus achieving the connection between the carrier and the movable element.

4. The device according to claim 3, wherein the sliding rail on the movable element is connected with the insertion piece.

5. The device according to claim 4, wherein the sliding rail on the movable element is connected with a positioning piece; the positioning piece is located in the chamber and driven by the sliding rail to slide on the sliding groove.

6. The device according to claim 5, wherein the movable element is a sheet structure; and the sliding rail and the positioning piece connected with the sliding rail are disposed at the top of the sheet structure; and the insertion piece is connected below the positioning piece; and the bolts are located at one end of the sheet structure.

7. The device according to claim 6, wherein when the carrier is located in the first position, the whole carrier is completely located in the chamber; when the carrier is located in the second position, a portion of the carrier stretches out of the chamber, thus contacting the fluid sample.

8. The device according to claim 7, wherein the device further comprises a testing element, and the testing element is located on the carrier.

9. The device according to claim 8, wherein the device further comprises an accommodating chamber and a sample collector; the accommodating chamber contains a treating fluid for treating the fluid sample; and the sample collector is fixedly connected with the chamber for receiving the testing element.

10. The device according to claim 9, wherein when the carrier is in the second position, the portion of the carrier stretching out of the chamber enters into the accommodating chamber, thus contacting the fluid sample in the accommodating chamber.

11. The device according to claim 10, wherein the fluid sample is sample dissolved or lysed by the fluid sample treating fluid collected by the sample collector.

12. The device according to claim 11, wherein the fluid sample collected by the sample collector comprises saliva, sputum, urine or nasal secretion.

13. The device according to claim 12, wherein the analyte comprises a drug small molecule, a viral antigen fragment or antibody.

* * * * *